(12) United States Patent
Ito

(10) Patent No.: US 11,006,792 B2
(45) Date of Patent: May 18, 2021

(54) TOILET LAYING MATERIAL AND TOILET

(71) Applicant: DAIKI CO., LTD., Tokyo (JP)

(72) Inventor: Hiroshi Ito, Tokyo (JP)

(73) Assignee: DAIKI CO., LTD., Tokyo (JP)

(*) Notice: Subject to any disclaimer, the term of this patent is extended or adjusted under 35 U.S.C. 154(b) by 430 days.

(21) Appl. No.: 15/986,365

(22) Filed: May 22, 2018

(65) Prior Publication Data

US 2018/0263437 A1    Sep. 20, 2018

Related U.S. Application Data

(63) Continuation of application No. PCT/JP2015/083853, filed on Dec. 2, 2015.

(51) Int. Cl.
| | | |
|---|---|---|
| *A47K 11/02* | (2006.01) |
| *A01K 23/00* | (2006.01) |
| *A01K 1/015* | (2006.01) |
| *A01N 25/10* | (2006.01) |
| *A61L 2/235* | (2006.01) |

(52) U.S. Cl.
CPC .............. *A47K 11/02* (2013.01); *A01K 1/015* (2013.01); *A01K 23/00* (2013.01); *A01N 25/10* (2013.01); *A61L 2/235* (2013.01); *Y02A 50/30* (2018.01)

(58) Field of Classification Search
CPC ....................................... A01K 23/00
USPC .................... 4/479, 449, 476; 297/188.09
See application file for complete search history.

(56) References Cited

FOREIGN PATENT DOCUMENTS

| | | |
|---|---|---|
| JP | 2003-180182 A | 7/2003 |
| JP | 2005-21071 A | 1/2005 |
| JP | 2005-110700 A | 4/2005 |

OTHER PUBLICATIONS

Jan. 19, 2016 Written Opinion issued in International Patent Application No. PCT/JP2015/083853.
Jan. 19, 2016 Search Report issued in International Patent Application No. PCT/JP2015/083853.

*Primary Examiner* — Lori L Baker
(74) *Attorney, Agent, or Firm* — Oliff PLC

(57) ABSTRACT

A toilet laying material is constituted by a granule. The granule is made of a chemically-integrated resin. A recess is formed in the surface of the granule.

19 Claims, 16 Drawing Sheets

TOILET LAYING MATERIAL AND TOILET

CROSS REFERENCE TO RELATED APPLICATION

This is a Continuation of International Application No. PCT/JP2015/083853 filed Dec. 2, 2015. The contents of this application are hereby incorporated by reference in their entirety.

TECHNICAL FIELD

The present invention relates to a granular toilet laying material, and to a toilet in which that laying material is laid down.

BACKGROUND ART

The toilet laying material disclosed in Patent Document 1 can be given as an example of a conventional toilet laying material. The toilet laying material disclosed in this document is constituted by a plurality of low-absorbency granules, and is laid down in a toilet for animal use. This toilet is partitioned into top and bottom parts by a partition member (a drainboard), and a plurality of the granules are laid out in the space above the partition member. An absorbent sheet is provided in the space below the partition member. According to the toilet configured in this manner, animal urine passes among the granules and through the partition member, and is then absorbed by the absorbent sheet.

CITATION LIST

Patent Document

Patent Document 1: JP 2003-180182A

SUMMARY OF INVENTION

Technical Problem

The above-described granules are obtained by compacting crushed material such as wood to form material into granular shape. These granules may partially or completely disintegrate when exposed to urine, and are thus not suited to repeated use over long periods of time. Accordingly, the conventional toilet laying material must be replaced frequently, which is not economical.

Solution to Problem

Having been achieved in light of the above-described problem, an object of the present invention is to provide a toilet laying material suited to repeated use over long periods of time, and a toilet in which such a laying material is laid out.

A toilet laying material according to the present invention is a toilet laying material constituted by a granule, wherein the granule is made of a chemically-integrated resin, and a recess is formed in a surface of the granule.

In the toilet laying material, the granule is made of a chemically-integrated resin, and thus does not disintegrate even when exposed to urine. As such, the toilet laying material is suited to repeated use over long periods of time.

Advantageous Effects of Invention

According to the present invention, a toilet laying material suited to repeated use over long periods of time, and a toilet in which such a laying material is laid out, are realized.

DESCRIPTION OF EMBODIMENTS

Figure 1:
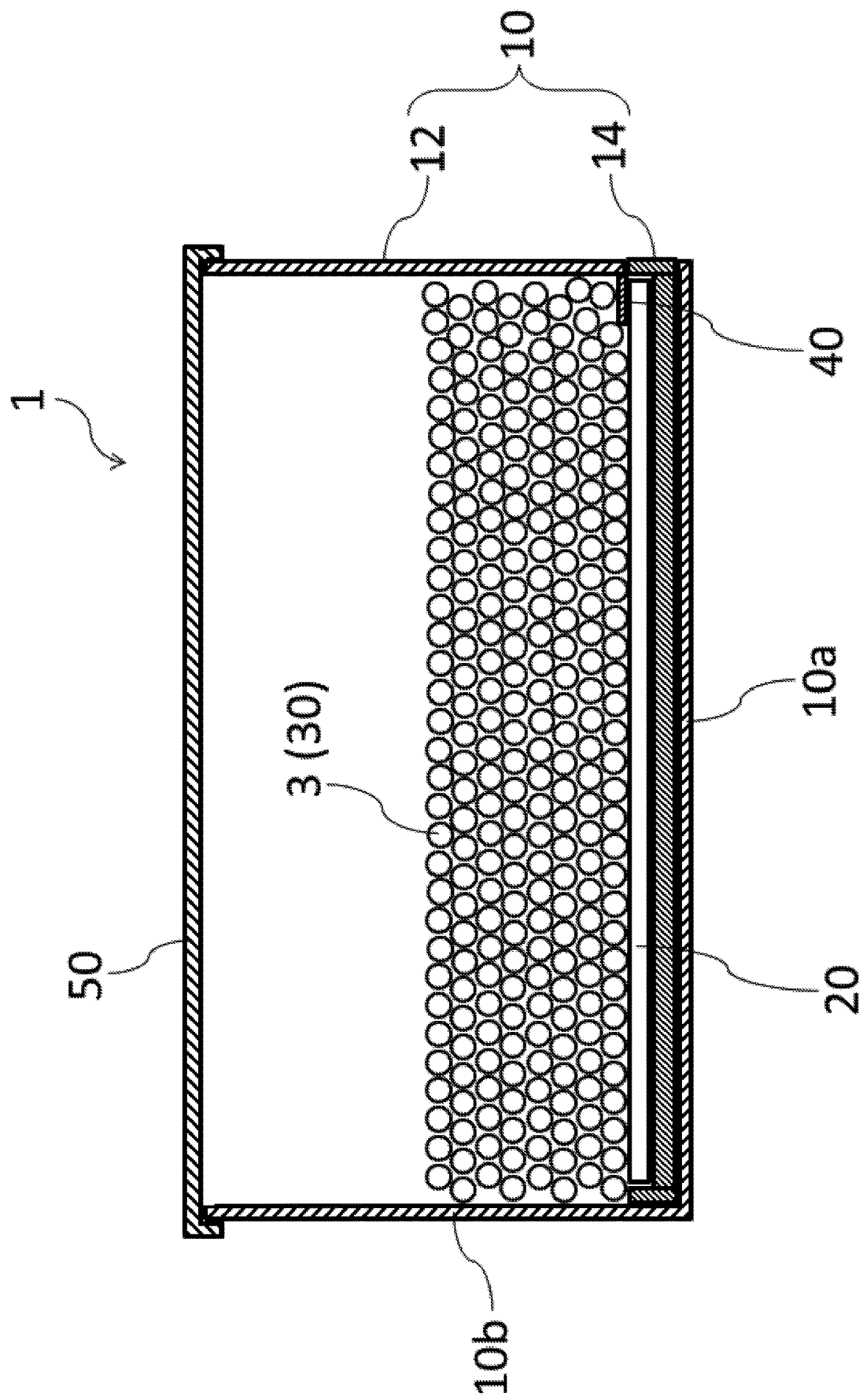
FIG. 1 is an end view illustrating a first embodiment of a toilet according to the present invention.

Embodiments of the present invention will be described in detail hereinafter with reference to the drawings. In the drawings, identical elements are given identical reference signs, and descriptions thereof will not be repeated.

First Embodiment

FIG. 1 is an end view illustrating a first embodiment of a toilet according to the present invention. A toilet 1 is a toilet for animal or human use, and includes a toilet laying material 3, a receptacle 10, and an absorbent sheet 20. The receptacle 10 has a bottom surface part 10a and side surface parts 10b. In the present embodiment, the receptacle 10 is substantially a parallelepiped. The receptacle 10 has a main body part 12 and a drawer part 14.

Figure 2:
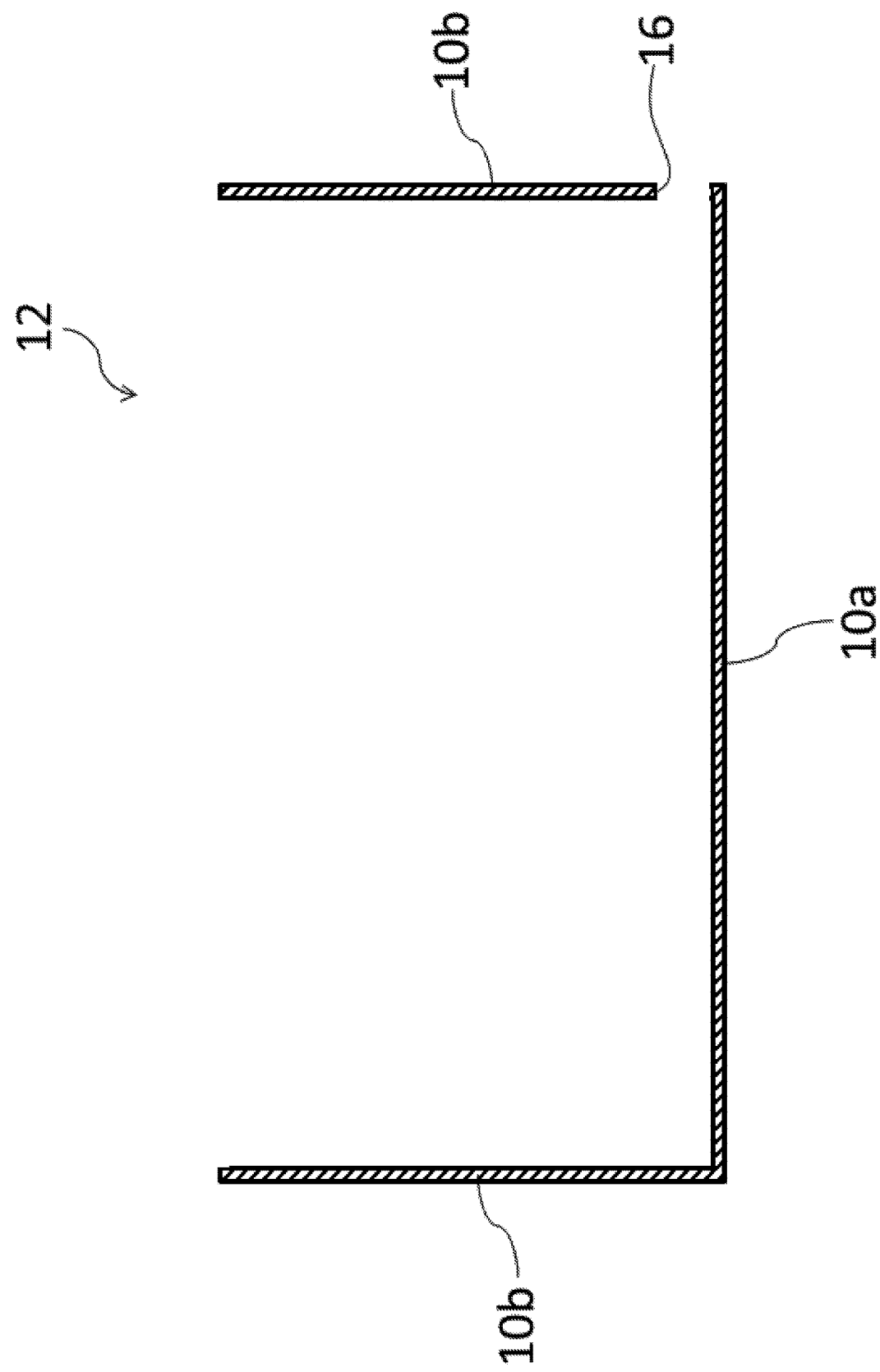
FIG. 2 is an end view illustrating a main body part of the toilet of FIG. 1.
Figure 3:
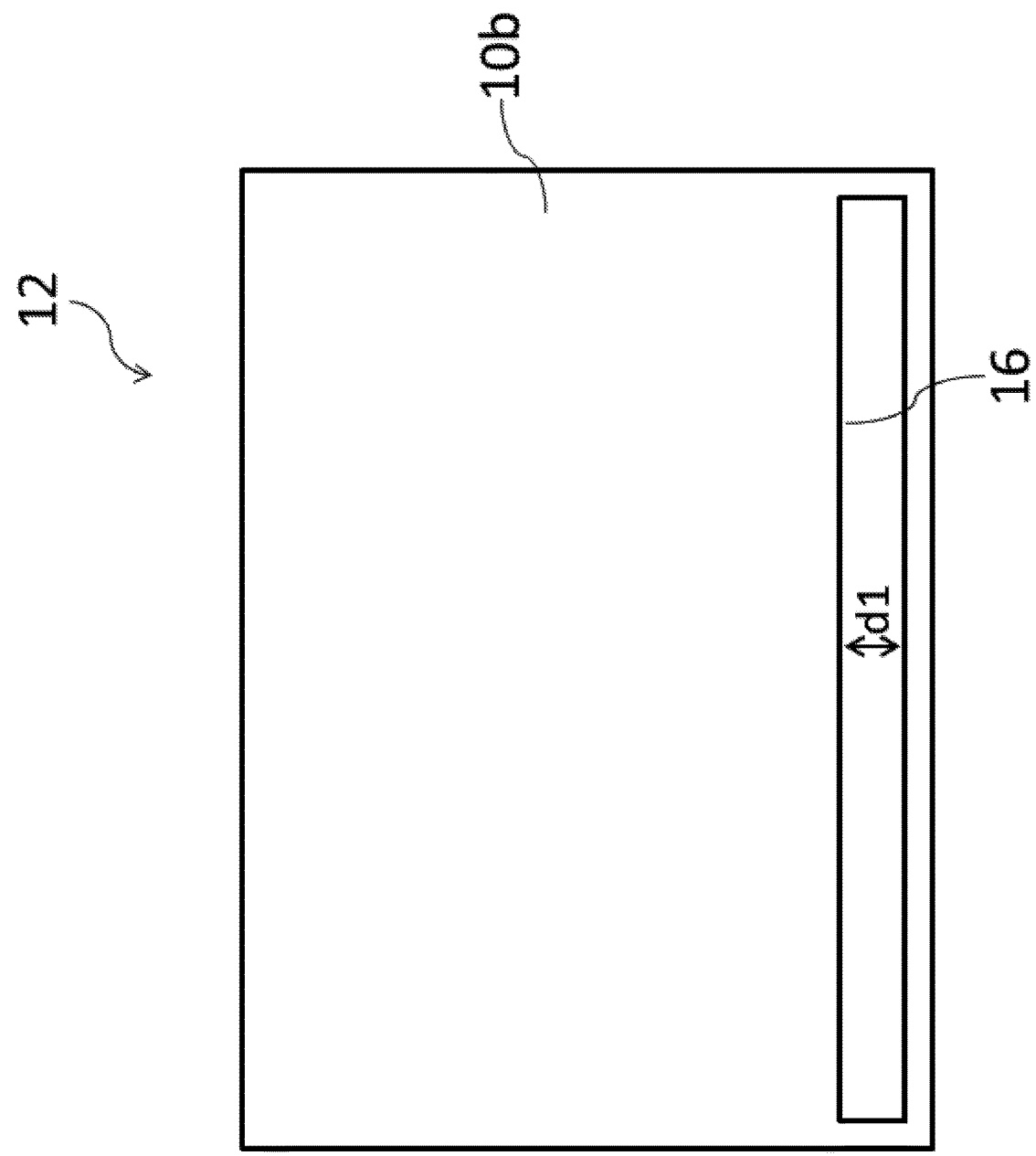
FIG. 3 is a front view of the main body part of the toilet of FIG. 1.

FIGS. 2 and 3 are an end view and a front view, respectively, of the main body part 12. The main body part 12 is a box-shaped part having the bottom surface part 10a and the side surface parts 10b. An opening 16 (a first opening) is formed in a side surface part 10b of the main body part 12. The opening 16 is located near the bottom surface part 10a, and is rectangular in shape. The length of the opening 16 in a left-right direction is substantially equal to the interior horizontal width of the main body part 12. Preferably, the length d1 of the opening 16 in an up-down direction (see FIG. 3) is less than or equal to 15 mm. A resin such as polypropylene or polyethylene can be used as the material of the main body part 12.

Figure 4:
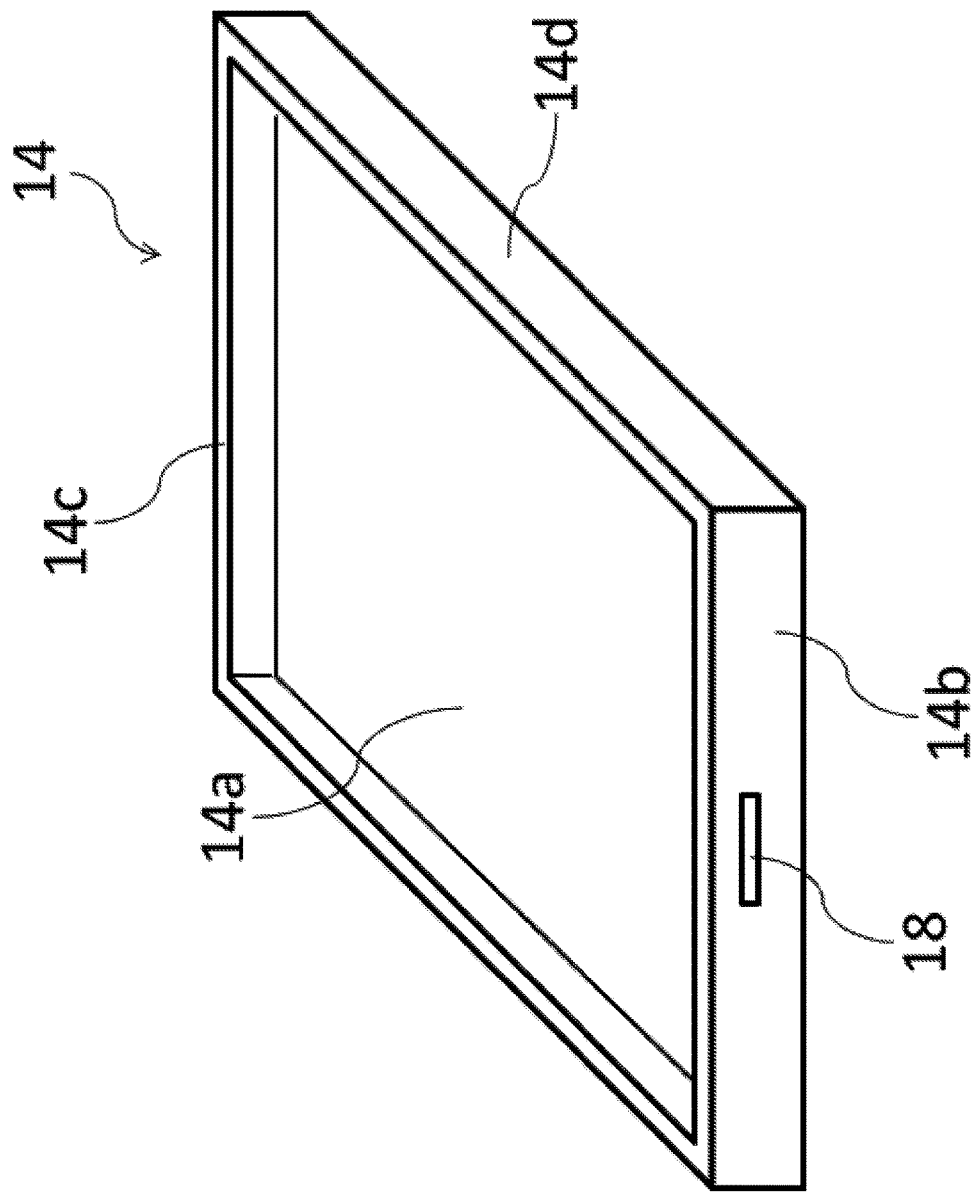
FIG. 4 is a perspective view of a drawer part of the toilet of FIG. 1.

FIG. 4 is a perspective view of the drawer part 14. The drawer part 14 can be pulled out from and inserted into the main body part 12 through the opening 16. The drawer part 14 has a base board 14a, a front board 14b, a rear board 14c, and a pair of side boards 14d. The size of the base board 14a is substantially equal to the size of the bottom surface part 10a of the main body part 12. The front board 14b is substantially the same shape and size as the opening 16. A grip 18 is attached to the front board 14b. A resin such as polypropylene or polyethylene can be used as the material of the drawer part 14.

Returning to FIG. 1, the absorbent sheet 20 is arranged within the receptacle 10. The absorbent sheet 20 is a sheet for absorbing urine. The absorbent sheet 20 is arranged within the receptacle 10 so as to be contained within the drawer part 14. At this time, the absorbent sheet 20 may be fixed to the base board 14a using double-sided tape or the like. Preferably, the height of the upper end of the front board 14b of the drawer part 14 is substantially equal to the height of the upper face of the absorbent sheet 20 contained within the drawer part 14, as illustrated in FIG. 1.

The toilet laying material 3 is further arranged within the receptacle 10. The toilet laying material 3 is arranged directly upon the absorbent sheet 20. The toilet laying material 3 is constituted by a plurality of granules 30. Each granule 30 is made of a chemically-integrated resin. In other words, the entirety of the resin constituting each the granule 30 is chemically integrated. A single mass formed by intertwining a plurality of resin pieces, a single mass formed by bonding a plurality of resin pieces together using a binder or the like, and so on do not constitute a "chemically-integrated resin".

Figure 5:
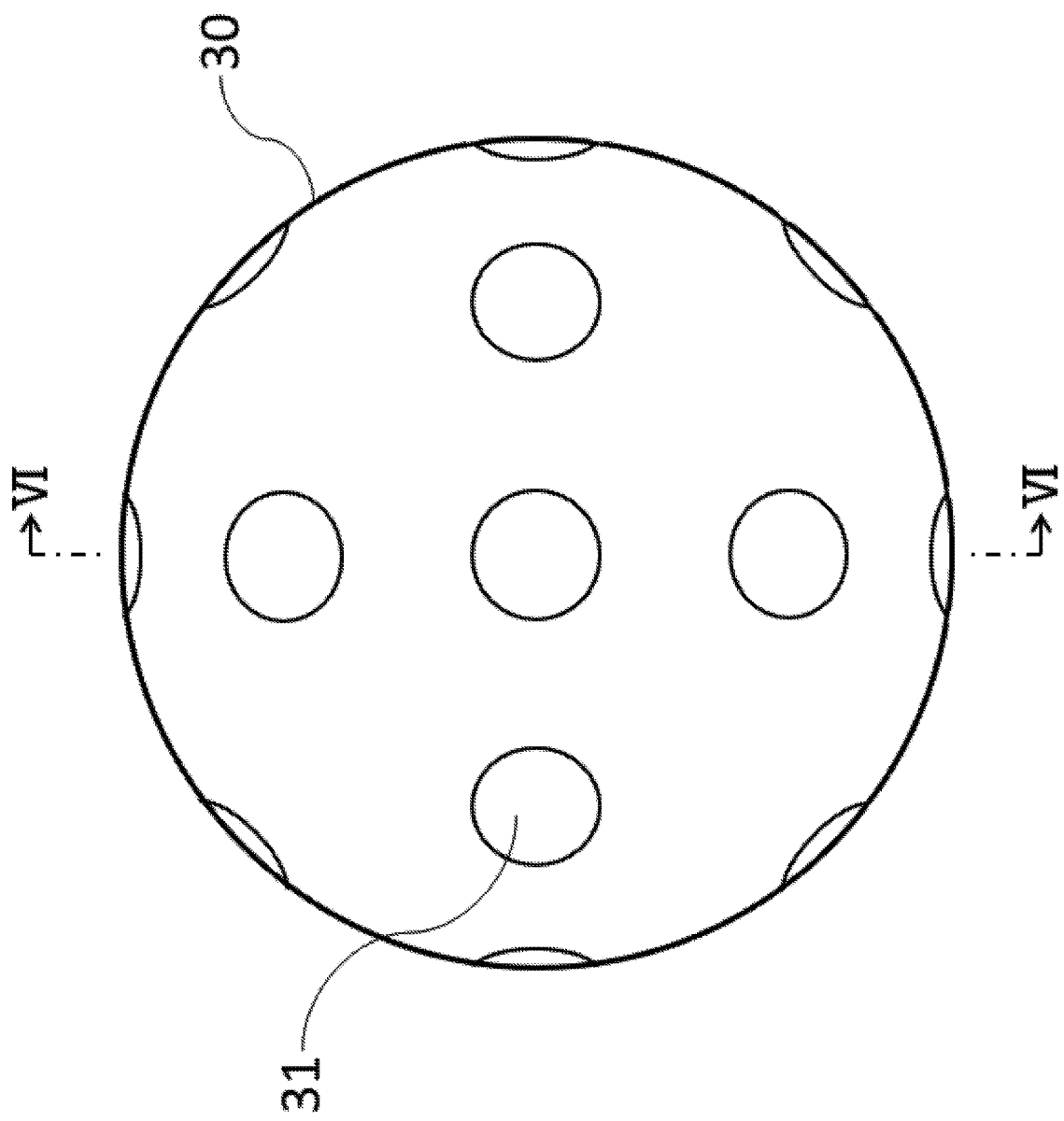
FIG. 5 is a front view illustrating an embodiment of a toilet laying material according to the present invention.
Figure 6:
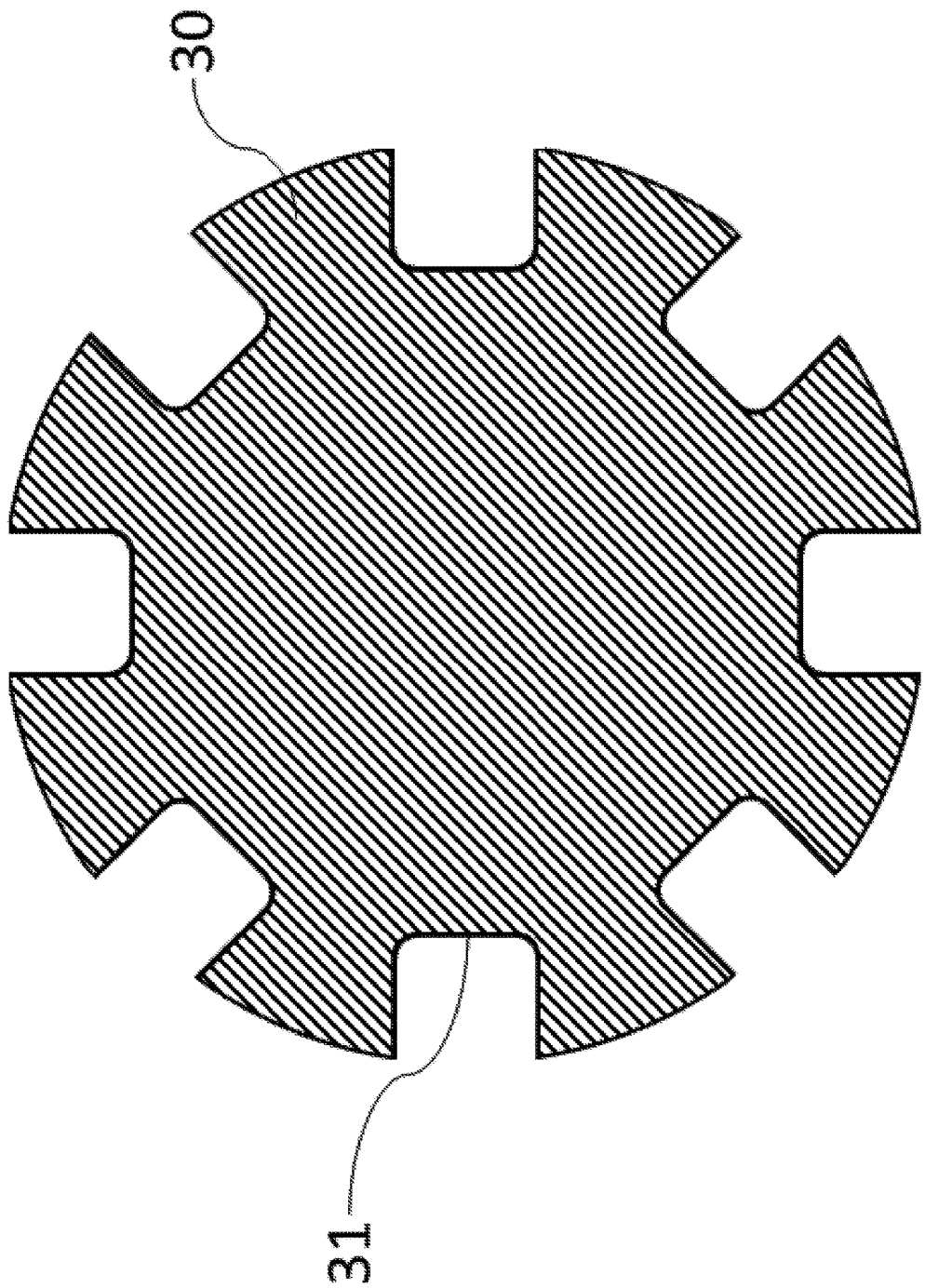
FIG. 6 is an end view taken along a line VI-VI in FIG. 5.

FIG. 5 is a front view of the granule 30. FIG. 6 is an end view taken along a line VI-VI in FIG. 5. A recess 31 is formed in the surface of the granule 30. In the present embodiment, a plurality of the recesses 31 are formed in the surface of the granule 30. The plurality of the recesses 31 are arranged regularly in the surface of the granule 30. The recesses 31 are provided at points across substantially the entire surface of the granule 30. Preferably, the depth of each of the recesses 31 is greater than or equal to 1 mm and less than or equal to 10 mm. Also, preferably, the diameter of the recess 31 in the surface of the granule 30 is greater than or equal to 1 mm and less than or equal to 3 mm. Note that the recesses 31 are not illustrated in FIG. 1.

A functional substance (not illustrated) is held within the recesses 31. The functional substance is a substance having a prescribed effect on air or urine within the receptacle 10. An antibacterial agent, an anti-odor agent, a deodorizing agent, a perfuming agent, and so on can be given as examples of the functional substance. The functional substance may be in liquid form or in solid form. The functional substance can be supplied into the recesses 31 by being injected into the recesses 31, for example.

In the present embodiment, the granules 30 are spherical. In other words, the granules 30 are spheres having the recesses 31 in their surfaces. The granules 30 are, for example, greater than or equal to 5 mm and less than or equal to 30 mm in diameter. The granules 30 may be hollow.

The granules 30 can be obtained by molding melted resin using a mold, as with injection molding or blow molding, for example. A resin such as polypropylene or polyethylene can be used as the material of the granules 30.

Figure 7:
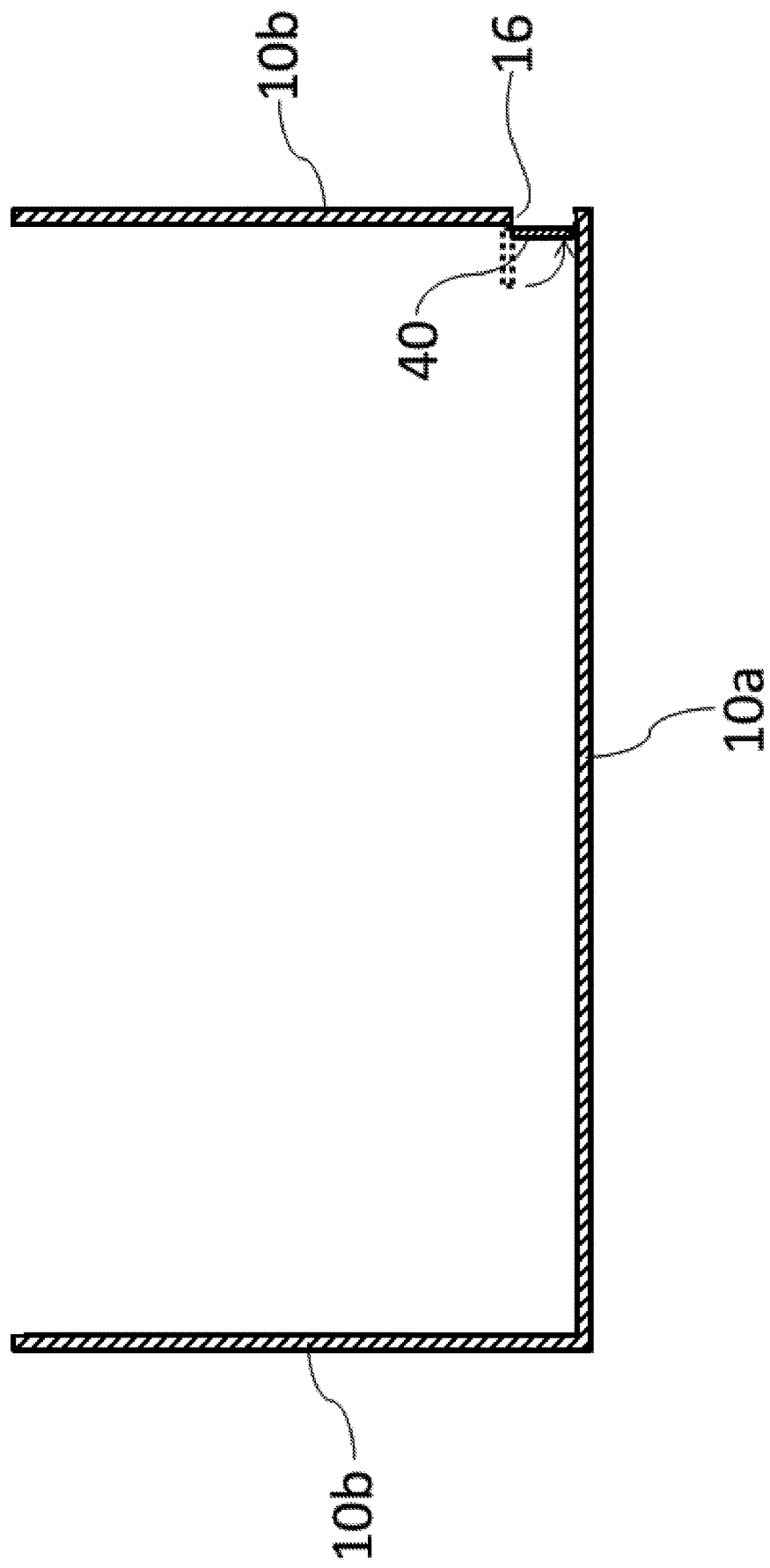
FIG. 7 is an end view illustrating the structure of an opening/closing part of the toilet of FIG. 1.

The toilet 1 further includes an opening/closing part 40 and a cover part 50. The opening/closing part 40 opens the opening 16 while the drawer part 14 is inserted into the main body part 12 (see FIG. 1). On the other hand, the opening/closing part 40 blocks the opening 16 after the drawer part 14 has been pulled out from the main body part 12, as illustrated in FIG. 7. In other words, the opening/closing part 40 is in a substantially vertical state when the drawer part 14 is not inserted into the main body part 12, but is pushed upward by the drawer part 14 into a substantially horizontal state when the drawer part 14 is inserted into the main body part 12. In the present embodiment, the opening/closing part 40 is constituted by a plate-shaped member (a first plate-shaped member) capable of pivoting with the upper side of the opening 16 serving as an axis. The opening/closing part 40 is attached to the upper side of the opening 16 by a hinge, for example. A resin such as polypropylene or polyethylene can be used as the material of the opening/closing part 40.

Figure 8:
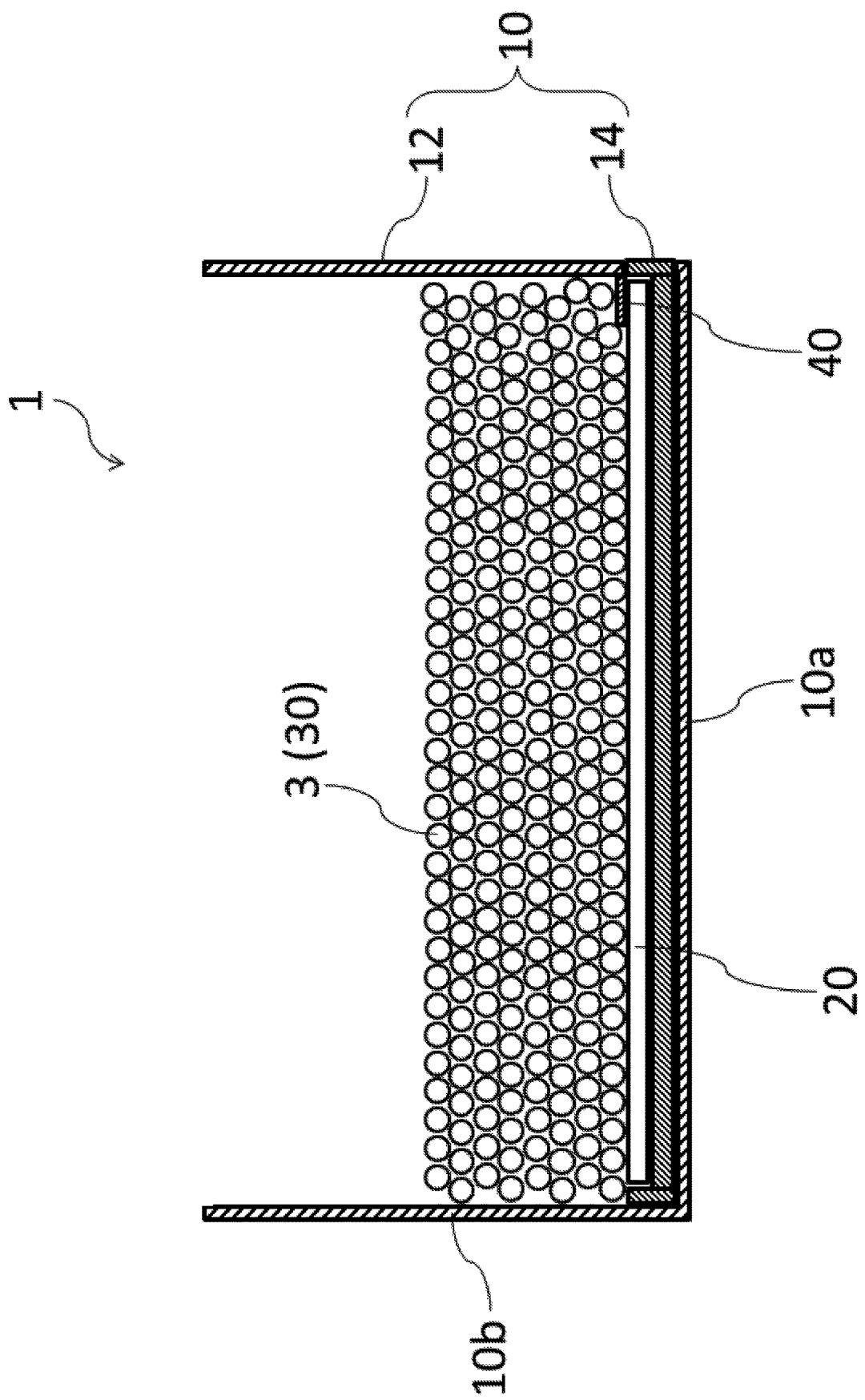
FIG. 8 is an end view illustrating a state of the toilet of FIG. 1 when in use.

The cover part 50 is a part that covers the receptacle 10 from above. The cover part 50 is provided so as to be openable and closable. The toilet 1 is used with the cover part 50 open, as illustrated in FIG. 8. The interior of the receptacle 10 is sealed when the cover part 50 is closed. A resin such as polypropylene or polyethylene can be used as the material of the cover part 50.

Effects of the present embodiment will be described. In the toilet laying material 3, the granules 30 are made of a chemically-integrated resin, and thus do not disintegrate even when exposed to urine. As such, the toilet laying material 3 is suited to repeated use over long periods of time.

Additionally, because the granules 30 are made of a chemically-integrated resin, the granules 30 absorb no urine. In other words, the granules 30 are completely nonabsorbent. With granules obtained by compacting crushed materials, as with the granules described in Patent Document 1, it is difficult to achieve complete nonabsorbency. This is because with such granules, gaps are present between the crushed materials even if a nonabsorbent material is used, and thus urine can penetrate through those gaps. The granules absorbing even a slight amount of urine causes not only the disintegration of the granules, but also produces odor. With respect to this point, according to the present embodiment, the granules 30 are completely nonabsorbent, and thus such odor can be prevented as well.

Furthermore, the recess 31 is formed in the surface of the granule 30. By holding various types of functional substances in the recess 31, the granule 30 having a desired function can be obtained with ease. In actuality, a functional substance is held within the recess 31 in the present embodiment. If the functional substance is an antibacterial agent, the propagation of various bacteria can be suppressed, even if urine adheres to the granule 30. If the functional substance is an anti-odor agent or a deodorizing agent, odors produced by urine can be eliminated. In addition, if the functional substance is a perfuming agent, odor produced by urine can be masked.

The recess 31 having a greater depth makes it possible for the recess 31 to hold a large amount of the functional substance. However, too great a depth reduces the mechanical strength of the granule 30. From this standpoint, preferably, the depth of the recess 31 is greater than or equal to 1 mm and less than or equal to 10 mm.

Reducing the diameter of the entrance of the recess 31, i.e., the diameter of the recess 31 in the surface of the granule 30, makes it difficult for the functional substance to leak out of the recess 31. This is because if the diameter of the recess 31 is small, a functional substance in liquid form tends to remain in the recess 31 due to surface tension. On the other hand, if the diameter is too small, it becomes difficult to insert the functional substance into the recess 31. From this standpoint, preferably, the diameter of the entrance of the recess 31 is greater than or equal to 1 mm and less than or equal to 3 mm.

A plurality of the recesses 31 are formed in the surface of the granule 30. Accordingly, a large amount of the functional substance with respect to the overall granule 30 can be held in the granule 30, even if the individual recesses 31 are made small.

The plurality of the recesses 31 are arranged regularly in the surface of the granule 30. In this case, compared to a case where the arrangement of the recesses 31 is irregular, the granule 30 can be formed with ease and the aesthetic appearance of the granule 30 can be enhanced.

The recesses 31 are provided at points across substantially the entire surface of the granule 30. Accordingly, the effects of the functional substance can be fully realized regardless of from which direction the granule 30 is exposed to urine.

The granules 30 are spherical in shape. In this case, the plurality of the granules 30 can be laid upon the absorbent sheet 20 at a high density. Accordingly, even if an odor emanates from the absorbent sheet 20 that has absorbed urine, that odor can be blocked by the granules 30 and kept from rising above the receptacle 10.

When the toilet 1 is used, urine expelled onto the toilet laying material 3 flows downward while passing through the gaps between adjacent granules 30, and reaches the absorbent sheet 20. The urine that has reached the absorbent sheet 20 is absorbed by the absorbent sheet 20. Here, as described above, the granules 30 are made of a chemically-integrated resin, and thus do not disintegrate even when exposed to urine.

However, conventional granules may partially or completely disintegrate when exposed to urine. If the disintegrated granules adhere to the absorbent sheet, the absorbent sheet will be soiled and the absorbency thereof will decrease. Thus in a conventional toilet provided with granules and an absorbent sheet, it is necessary to provide a partition member to keep the granules and the absorbent sheet separated. However, providing such a partition member complicates the structure of the toilet.

With respect to this point, in the toilet 1, the granules 30 do not disintegrate. Thus a drop in the absorbency of the absorbent sheet 20 can be prevented even if the granules 30 and the absorbent sheet 20 are not separated. In actuality, the granules 30 are arranged directly upon the absorbent sheet 20. Thus with the toilet 1, it is not necessary to provide a partition member for separating the granules 30 and the absorbent sheet 20 during use. As such, the toilet 1, which does not require a partition member despite both the granules 30 and the absorbent sheet 20 being provided, can be realized.

In the toilet 1, the drawer part 14 is provided capable of being pulled out from and pushed into the main body part 12 through the opening 16. This makes it easy to replace a used absorbent sheet 20 with a new one.

The front board 14b of the drawer part 14 is substantially the same shape and size as the opening 16. Accordingly, the entire opening 16 is blocked off by the front board 14b, which makes it possible to prevent urine from leaking out of the receptacle 10 through the opening 16.

If the height of the upper end of the front board 14b of the drawer part 14 is substantially equal to the height of the upper surface of the absorbent sheet 20 contained in the drawer part 14, there is no gap between the upper surface of the absorbent sheet 20 and the opening 16 when the drawer part 14 is pulled out from the main body part 12. This makes it possible to prevent the granules 30 from escaping from the receptacle 10 through the opening 16, becoming trapped between the upper surface of the absorbent sheet 20 and the opening 16, and so on.

Reducing the length d1 of the opening 16 (see FIG. 3) makes it difficult for the granules 30 to escape from the receptacle 10. From this standpoint, the length d1 is preferably less than or equal to 15 mm.

The toilet 1 is provided with the opening/closing part 40. Accordingly, the opening 16 is blocked off after the drawer part 14 is pulled out from the main body part 12, which prevents the granules 30 from escaping from the receptacle 10.

The opening/closing part 40 is constituted by a plate-shaped member capable of pivoting with the upper side of the opening 16 serving as an axis. Accordingly, the opening/closing part 40, which opens the opening 16 when the drawer part 14 is inserted into the main body part 12 and blocks off the opening 16 after the drawer part 14 has been pulled out from the main body part 12, can be realized with a simple structure.

Figure 9:
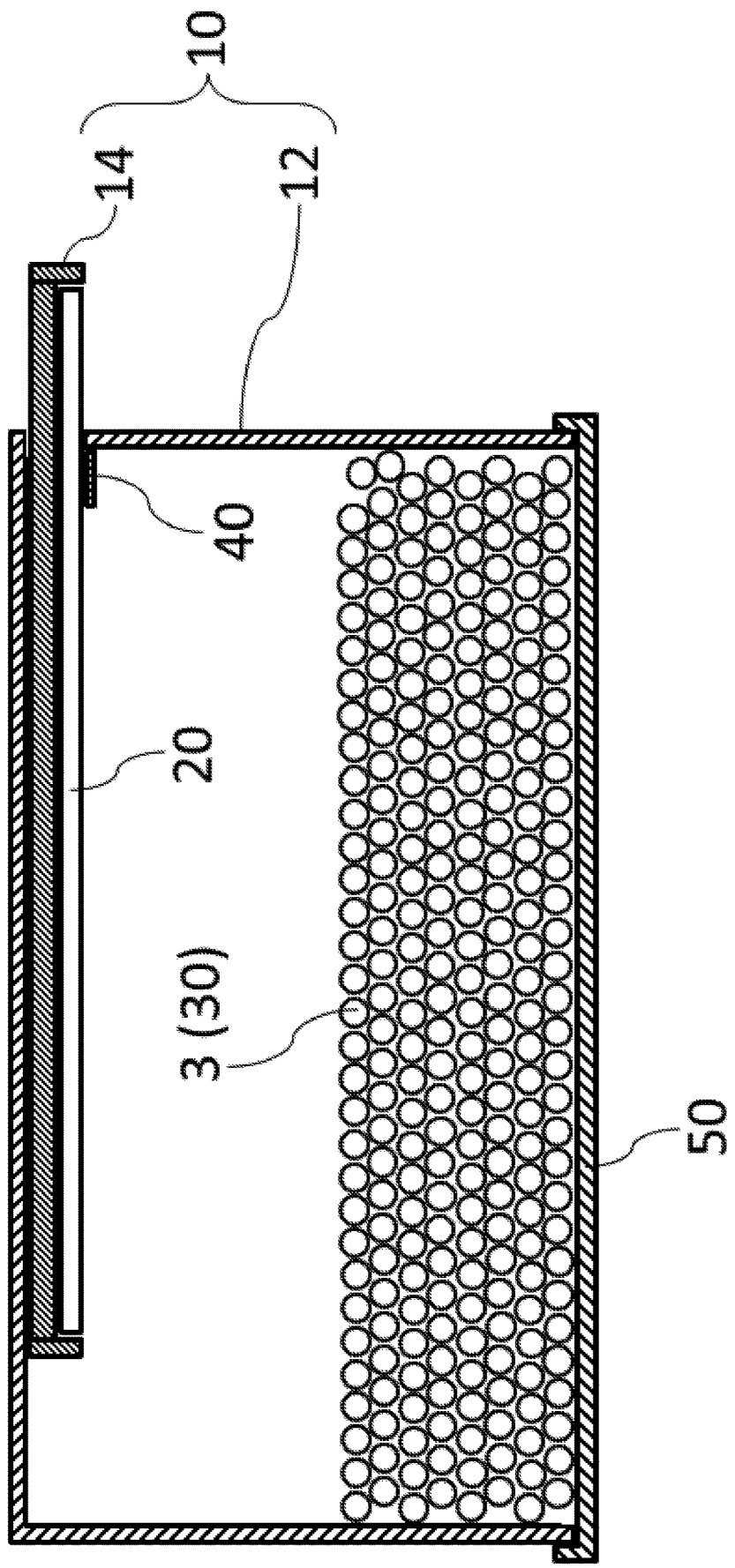
FIG. 9 is an end view illustrating an effect of the toilet of FIG. 1.

The cover part 50, which covers the receptacle 10 from above, is provided. By closing the cover part 50 when the toilet 1 is not in use, odor arising within the receptacle 10 can be prevented from escaping to the exterior of the receptacle 10. Additionally, when the absorbent sheet 20 is to be replaced, inverting the receptacle 10 after closing the cover part 50, as illustrated in FIG. 9, causes the granules 30 to separate from the absorbent sheet 20, which makes it possible to pull out and insert the drawer part 14 smoothly.

Second Embodiment

Figure 10:
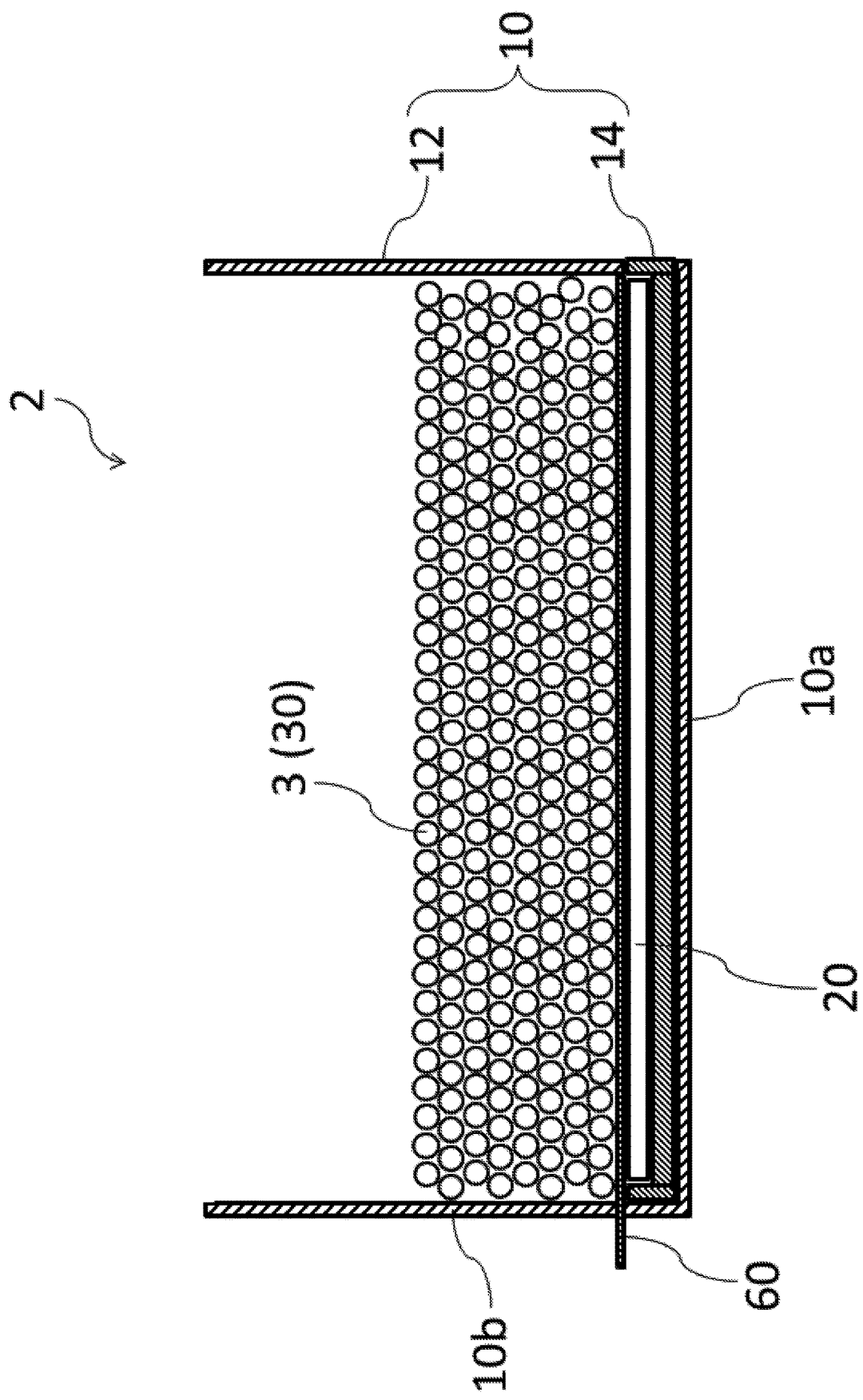
FIG. 10 is an end view illustrating a second embodiment of a toilet according to the present invention.

FIG. 10 is an end view illustrating a second embodiment of a toilet according to the present invention. A toilet 2 is a toilet for animal or human use, and includes a plate-shaped member 60 (a second plate-shaped member) in addition to the toilet laying material 3, the receptacle 10, and the absorbent sheet 20. The configurations of the toilet laying material 3 and the absorbent sheet 20 are as described in the first embodiment.

Figure 11:
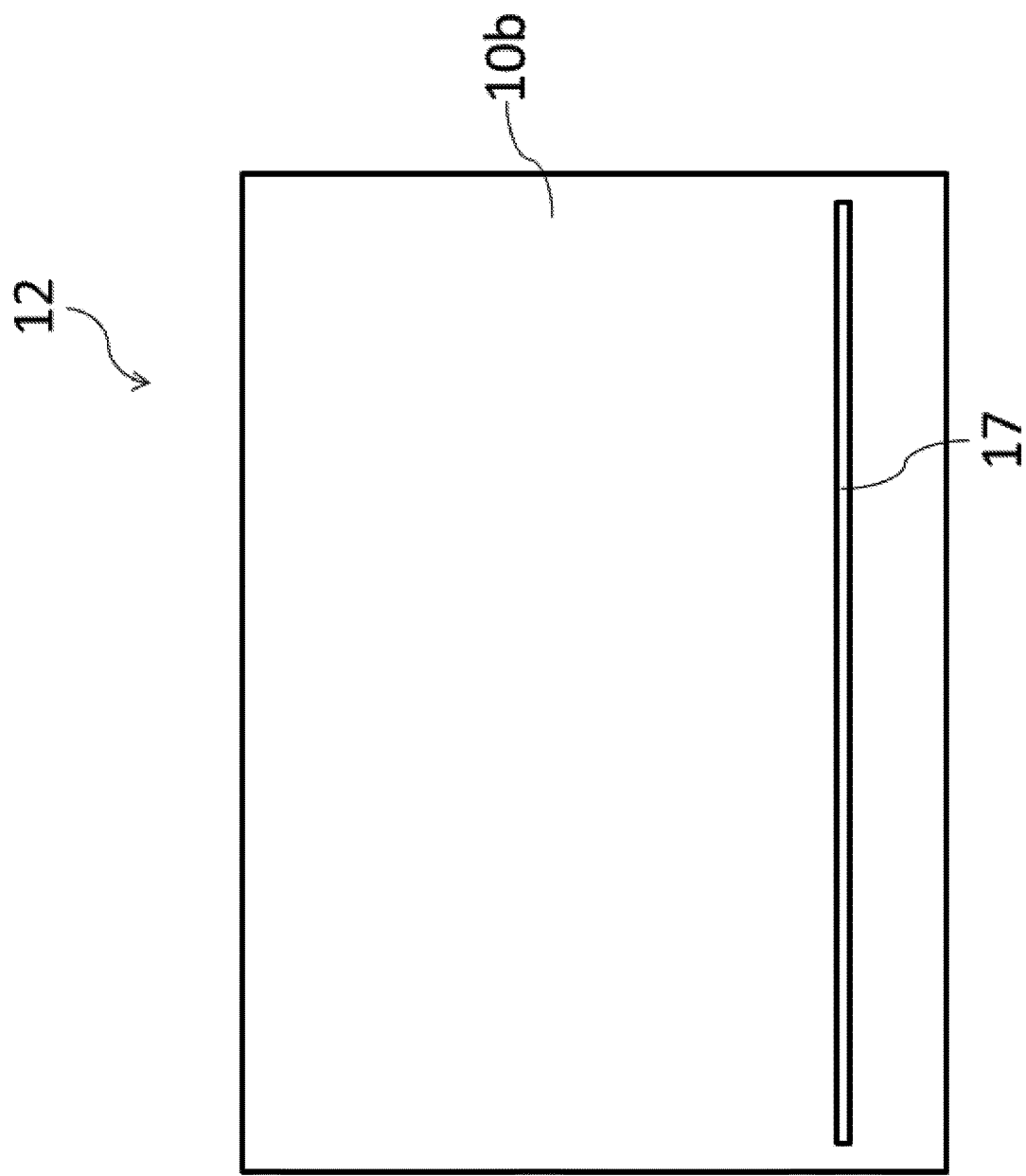
FIG. 11 is a rear view of a main body part of the toilet of FIG. 10.

FIG. 11 is a rear view of the main body part 12 according to the present embodiment. An opening 17 (a second opening) is formed in a side surface part 10b of the main body part 12. The opening 17 is provided on the side opposite from the opening 16. The length of the opening 17 in the left-right direction is substantially equal to the interior horizontal width of the main body part 12. The height of the lower side of the opening 17 is substantially equal to the height of the upper side of the opening 16. An opening/closing part (not illustrated) having the same functionality as the opening/closing part 40 is provided in the opening 17 as well. The other configurations of the main body part 12 are as described in the first embodiment.

Figure 12:
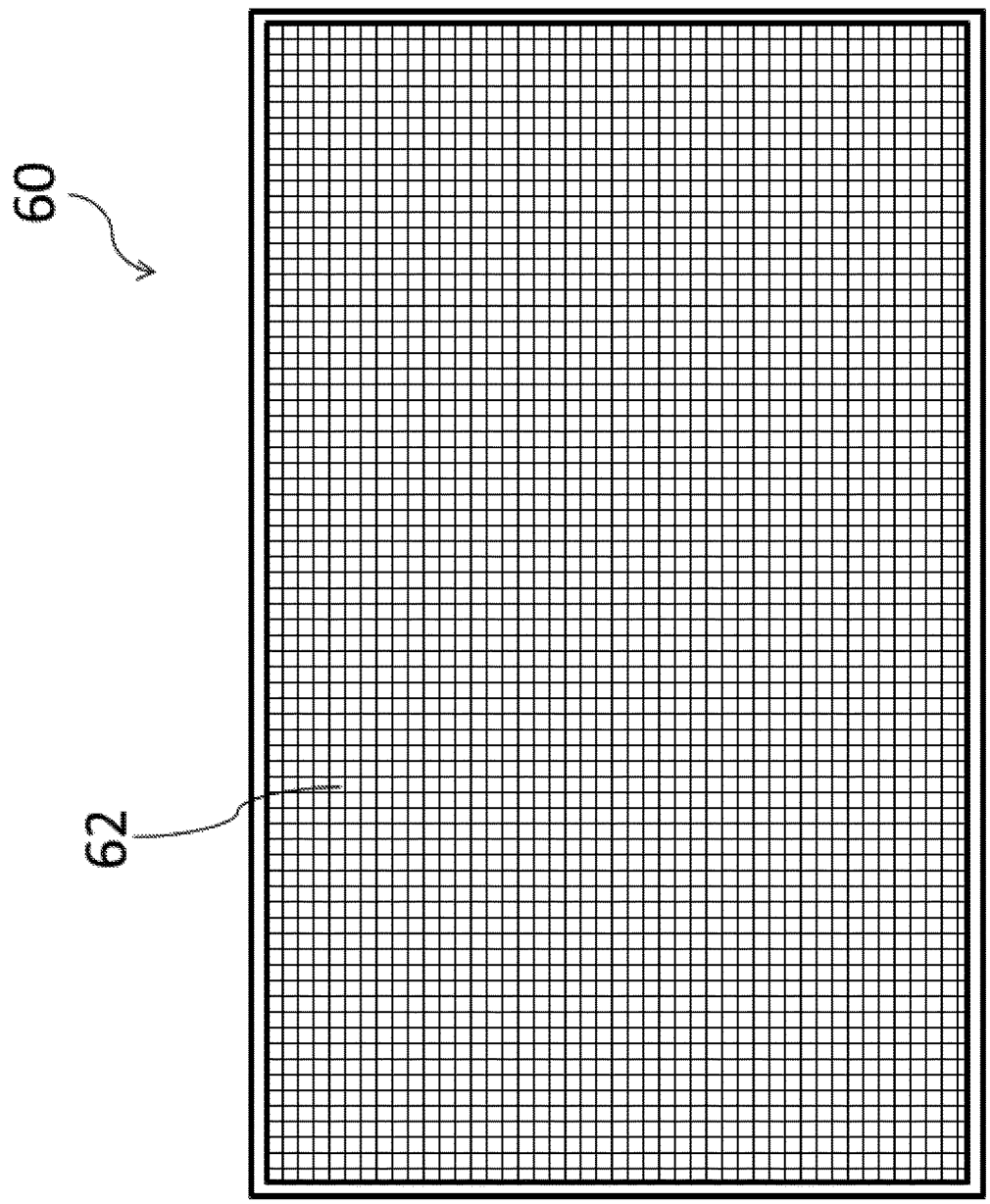
FIG. 12 is a plan view of a plate-shaped member of the toilet of FIG. 10.

FIG. 12 is a plan view of the plate-shaped member 60. A plurality of holes 62 are formed in the plate-shaped member 60. In the present embodiment, the plate-shaped member 60 is a wire mesh, and the openings in the mesh constitute the holes 62. The holes 62 have a size that prevents the toilet laying material 3 (the granules 30) from passing therethrough. The plate-shaped member 60 has a size that covers substantially the entire bottom surface part 10a of the main body part 12 when interposed between the absorbent sheet 20 and the toilet laying material 3 as described later. Preferably, the thickness of the plate-shaped member 60 is less than or equal to 5 mm.

Figure 13:
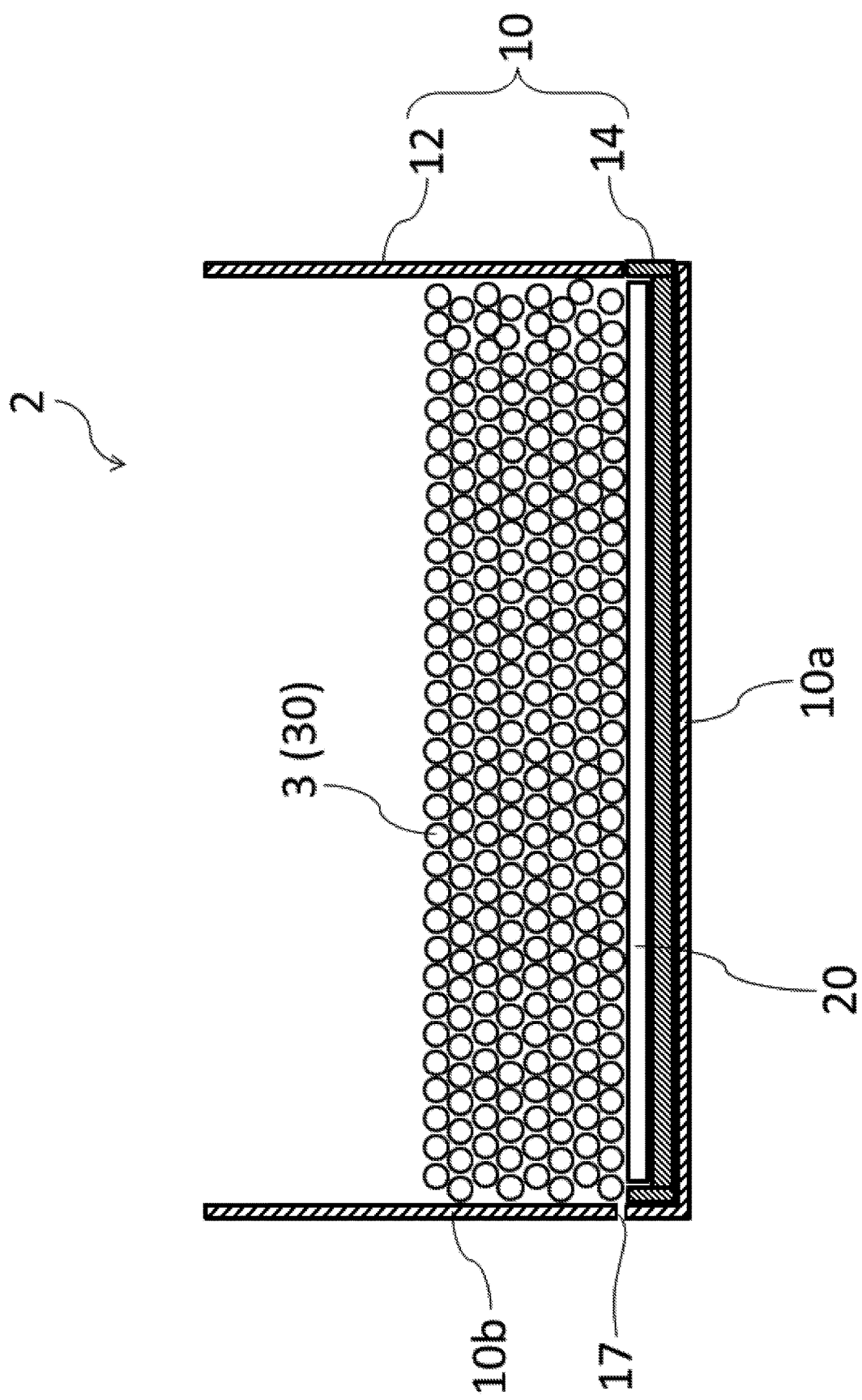
FIG. 13 is an end view illustrating a state of the toilet of FIG. 10 when in use.

The plate-shaped member 60 can be pulled out from and inserted into the main body part 12 through the opening 17. The toilet 2 is used with the plate-shaped member 60 pulled out from the main body part 12, as illustrated in FIG. 13. The plate-shaped member 60 is inserted into the main body part 12 as necessary when the toilet 2 is not in use. At this time, the plate-shaped member 60 is inserted between the absorbent sheet 20 and the toilet laying material 3 with the absorbent sheet 20 and the toilet laying material 3 remaining within the receptacle 10. As a result, the plate-shaped member 60 is interposed between the absorbent sheet 20 and the toilet laying material 3 (see FIG. 10).

Effects of the present embodiment will be described. The toilet 2 is provided with the plate-shaped member 60. Inserting the plate-shaped member 60 into the main body part 12 before replacing the absorbent sheet 20 separates the toilet laying material 3 from the absorbent sheet 20, which makes it possible to pull out and insert the drawer part 14 smoothly.

The opening 17 is formed in a side surface part 10b of the main body part 12. Accordingly, even if the absorbent sheet 20 and the toilet laying material 3 remain within the receptacle 10, the plate-shaped member 60 can easily be inserted between the absorbent sheet 20 and the toilet laying material 3.

The holes 62 are formed in the plate-shaped member 60. Accordingly, after the drawer part 14 has been removed from the main body part 12, the granules 30 can be rinsed with water from above with the granules 30 remaining on the plate-shaped member 60. As a result, the granules 30 can be cleaned with ease while remaining contained within the receptacle 10.

Reducing the thickness of the plate-shaped member 60 makes it easy to insert the plate-shaped member 60 between the absorbent sheet 20 and the toilet laying material 3. From this standpoint, preferably, the thickness of the plate-shaped member 60 is less than or equal to 5 mm.

The plate-shaped member 60 is a wire mesh. A wire mesh is both thin and sufficiently rigid, and is therefore suitable for use as the plate-shaped member 60 that can easily be inserted between the absorbent sheet 20 and the toilet laying material 3. Other effects of the present embodiment are the same as those of the first embodiment.

Figure 14:
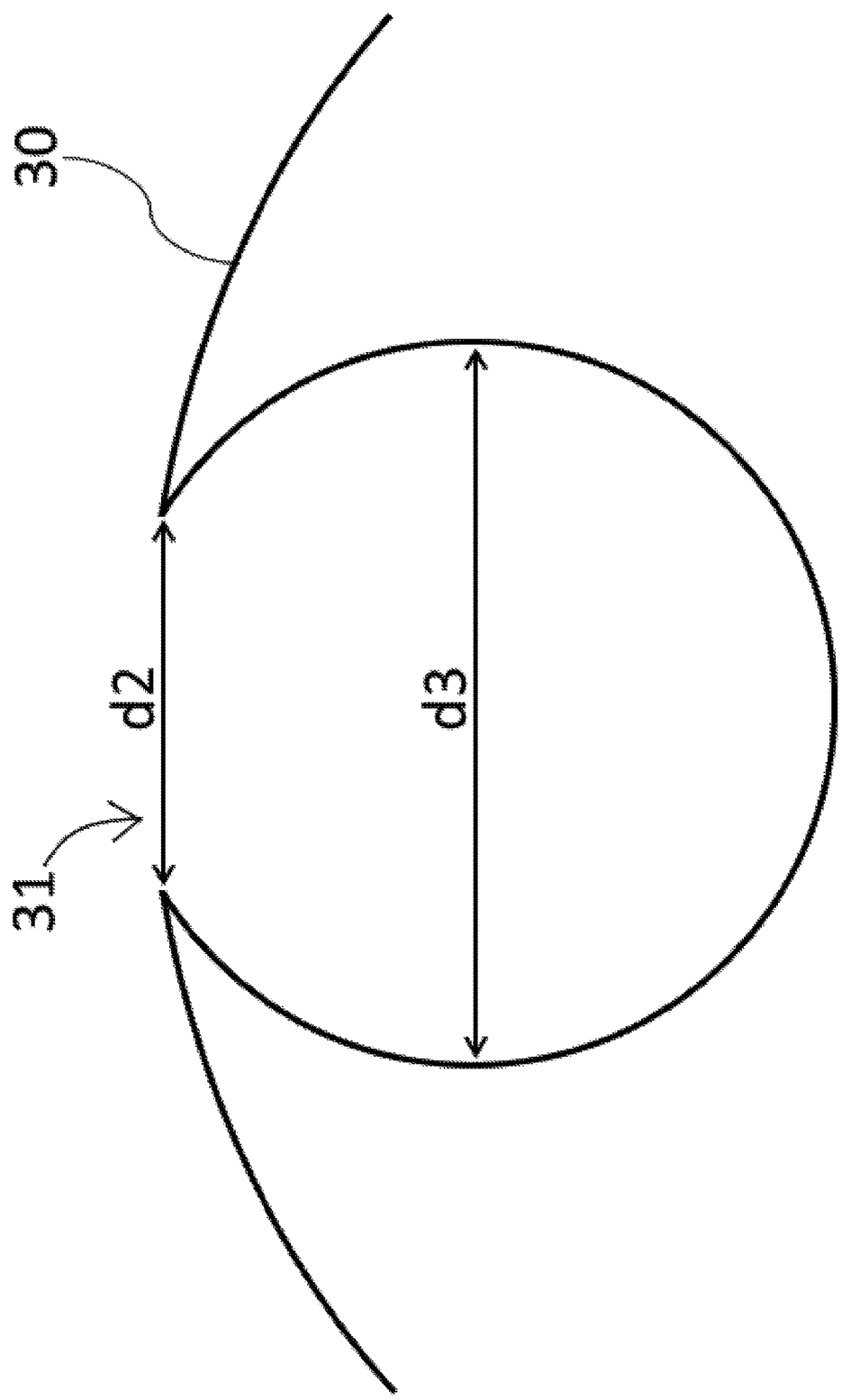
FIG. 14 is a diagram illustrating a variation on a recess.

The present invention is not limited to the foregoing embodiments, and many variations can be made thereon. For example, the diameter d2 of the recess 31 in the surface of the granule 30 may be smaller than the maximum diameter d3 of the recess 31, as illustrated in FIG. 14. In this manner, by employing a bulging shape for the interior of the recess 31, a large amount of the functional substance can be held within the recess 31 even if the diameter of the entrance of the recess 31 (the diameter d2) is not large.

Figure 15:
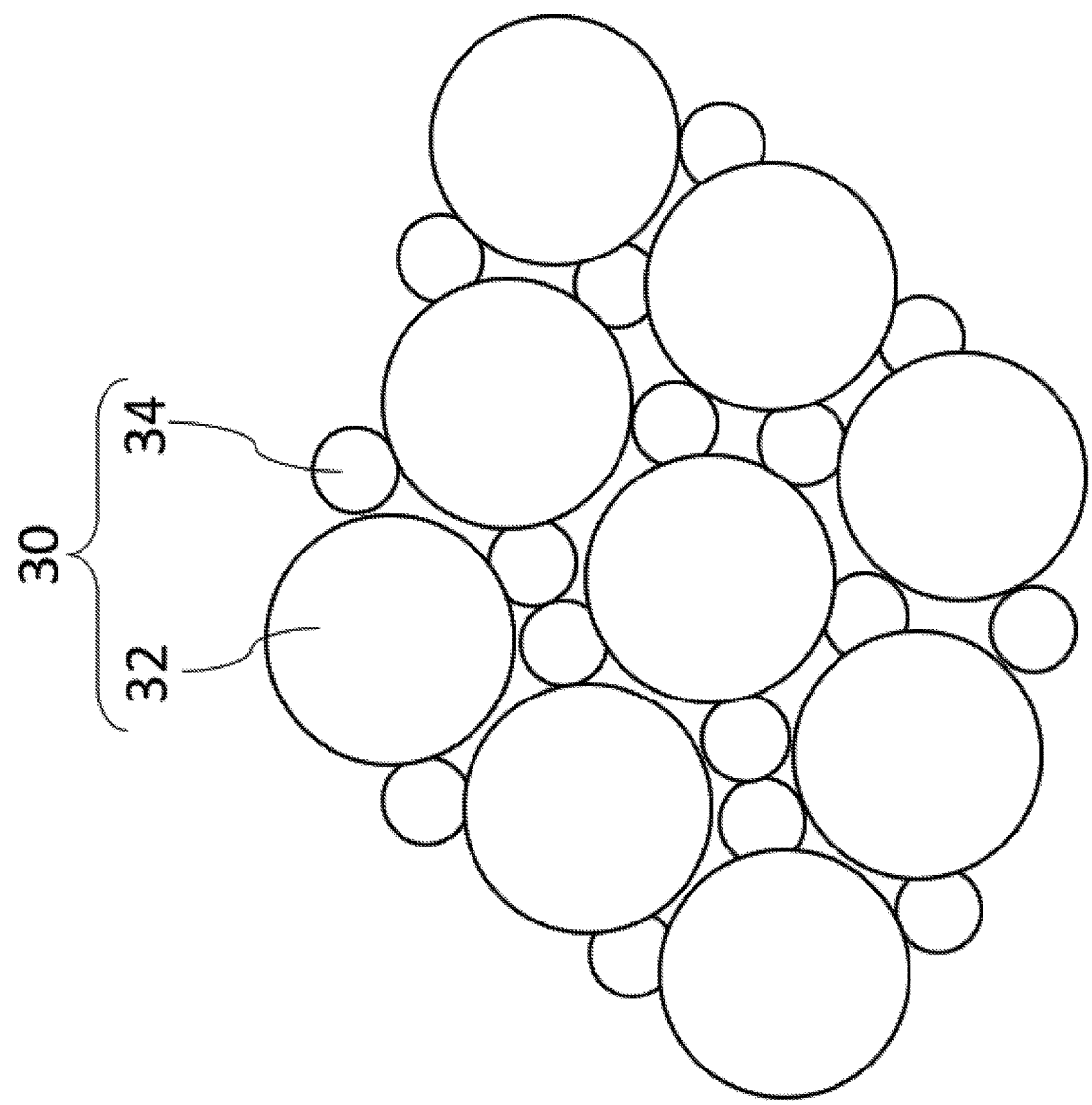
FIG. 15 is a diagram illustrating a variation on a granule.

Additionally, in the foregoing embodiments, the plurality of the granules 30 may include a granule 32 (first granule) and a granule 34 (second granule) having different sizes, as illustrated in FIG. 15. The granule 32 has a first diameter, and the granule 34 has a second diameter smaller than the first diameter. Preferably, the first diameter is less than or equal to 30 mm. Preferably, the second diameter is greater than or equal to 5 mm.

In this case, the granules 34 enter into the gaps between the granules 32, which makes it possible to lay out the granules 30 at a higher density than when the granules 30 include only the granules 32. Laying out the granules 30 at a high density in this manner makes it possible to keep an animal from sinking in when the animal steps onto the granules 30. This stabilizes the animal's footing, which reduces the burden on the animal's legs when the animal excretes.

Figure 16:
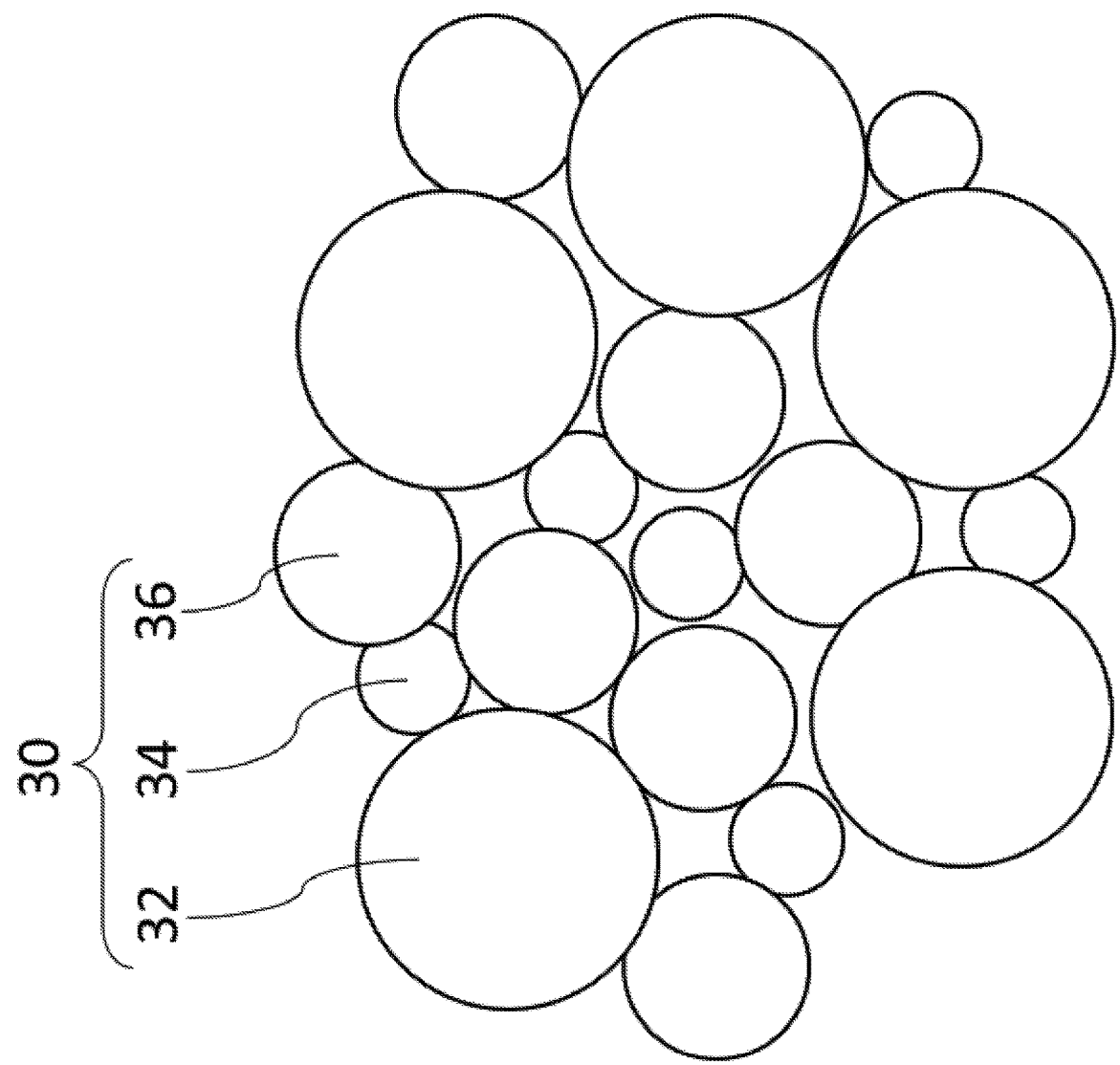
FIG. 16 is a diagram illustrating another variation on a granule.

Furthermore, the plurality of the granules 30 may include a granule 36 (third granule) in addition to the granule 32 and the granule 34, as illustrated in FIG. 16. The granule 36 has a third diameter. The third diameter is smaller than the first diameter and greater than the second diameter. In this case, the granules 36 enter into the gaps between the granules 32 and the gaps between the granules 32 and the granules 34. This makes it possible to increase the density of the granules 30 even further. Note that the recesses formed in the granules 32, 34, and 36 are not illustrated in FIGS. 15 and 16.

The foregoing embodiments describe examples in which a plurality of the recesses 31 are formed in the surface of the granule 30. However, only one recess 31 may be formed in the surface of the granule 30.

In the foregoing embodiments, a material aside from resin may be added to the granule 30 as long as the chemical integrity of the resin is not lost. In this case, however, the weight percentage of the material aside from the resin in the granule 30 is preferably less than or equal to 10% (that is, the weight percentage of chemically-integrated resin is greater than or equal to 90%).

The foregoing embodiments describe a case where the granules 30 are spherical. However, the shape of the granule 30 may be a shape aside from a sphere (e.g., a cylinder, an ellipsoid, a cube, a regular tetrahedron, or the like) as long as the granule 30 is granular.

The foregoing embodiments describe examples in which the toilet laying material 3 is arranged directly upon the absorbent sheet 20. However, the toilet laying material 3 may be arranged so as to be separated from the absorbent sheet 20 within the receptacle 10. For example, a partition member may be provided within the receptacle 10, with the toilet laying material 3 arranged in a space above the partition member and the absorbent sheet 20 arranged in a space below the partition member.

The foregoing embodiments describe examples in which the absorbent sheet 20 is arranged within the receptacle 10. However, it is not absolutely necessary to provide the absorbent sheet 20. Only the toilet laying material 3 may be arranged within the receptacle 10.

LIST OF REFERENCE NUMERALS

1 Toilet
2 Toilet
3 Toilet laying material
10 Receptacle
10a Bottom surface part
10b Side surface part
12 Main body part
14 Drawer part
14a Base board
14b Front board
14c Rear board
14d Side board
16 Opening (first opening)
17 Opening (second opening)
18 Grip
20 Absorbent sheet
30 Granule
31 Recess 32 Granule (first granule)
34 Granule (second granule)
36 Granule (third granule)
40 Opening/closing part
50 Cover part
60 Plate-shaped member (second plate-shaped member)
62 Hole

The invention claimed is:

1. A toilet laying material constituted by a granule,
wherein the granule is made of a chemically-integrated resin; and
a recess within which a functional substance in liquid form is held is formed in a surface of the granule.

2. The toilet laying material according to claim 1,
wherein the functional substance is an antibacterial agent.

3. The toilet laying material according to claim 1,
wherein the functional substance is an anti-odor agent or a deodorizing agent.

4. The toilet laying material according to claim 1,
wherein the functional substance is a perfuming agent.

5. The toilet laying material according to claim 1,
wherein a diameter of the recess in the surface of the granule is smaller than a maximum diameter of the recess.

6. The toilet laying material according to claim 1,
wherein the granule is spherical in shape.

7. The toilet laying material according to claim 1,
wherein a plurality of the recesses are formed in the surface of the granule.

8. The toilet laying material according to claim 7,
wherein the plurality of the recesses are arranged regularly in the surface of the granule.

9. The toilet laying material according to claim 7,
wherein the plurality of recesses are provided at points across substantially the entire surface of the granule.

10. The toilet laying material according to claim 1,
wherein the toilet laying material is constituted by a plurality of the granules; and
the plurality of the granules include a first granule having a first diameter and a second granule having a second diameter smaller than the first diameter.

11. The toilet laying material according to claim 10,
wherein the plurality of the granules include a third granule having a third diameter smaller than the first diameter and greater than the second diameter.

12. A toilet comprising:
a receptacle having a bottom surface part and a side surface part; and
the toilet laying material according to claim 1, provided within the receptacle.

13. The toilet according to claim 12, further comprising:
an absorbent sheet provided within the receptacle,
wherein the toilet laying material is arranged directly upon the absorbent sheet.

14. The toilet according to claim 13,
wherein the receptacle has a main body part having the bottom surface part and the side surface part, and a drawer part containing the absorbent sheet;
a first opening is formed in the side surface part of the main body part; and
the drawer part can be pulled out from and inserted into the main body part through the first opening.

15. The toilet according to claim 14,
wherein a height of an upper end of a front board of the drawer part is substantially equal to a height of an upper surface of the absorbent sheet contained in the drawer part.

16. The toilet according to claim 14, further comprising:
an opening/closing part that opens the first opening when the drawer part is inserted into the main body part, and blocks off the first opening after the drawer part has been pulled out from the main body part.

17. The toilet according to claim 14, further comprising:
a plate-shaped member inserted between the absorbent sheet and the toilet laying material in a state where the absorbent sheet and the toilet laying material are present within the receptacle.

18. The toilet according to claim 17,
wherein a second opening is formed in the side surface part of the main body part; and
the plate-shaped member can be pulled out from and inserted into the main body part through the second opening.

19. The toilet according to claim 12, further comprising:
a cover part that covers the receptacle from above.

* * * * *